US011697832B2

(12) United States Patent
Lee et al.

(10) Patent No.: US 11,697,832 B2
(45) Date of Patent: Jul. 11, 2023

(54) FRUCTOSE-C4-EPIMERASE AND METHOD OF PRODUCING TAGATOSE USING THE SAME

(71) Applicant: CJ CHEILJEDANG CORPORATION, Seoul (KR)

(72) Inventors: Young Mi Lee, Seoul (KR); Il Hyang Park, Seoul (KR); Seong Bo Kim, Seoul (KR); Seung Won Park, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/280,792

(22) PCT Filed: Aug. 23, 2019

(86) PCT No.: PCT/KR2019/010734
§ 371 (c)(1),
(2) Date: Mar. 26, 2021

(87) PCT Pub. No.: WO2020/067649
PCT Pub. Date: Apr. 2, 2020

(65) Prior Publication Data
US 2022/0002770 A1 Jan. 6, 2022

(30) Foreign Application Priority Data

Sep. 27, 2018 (KR) ........................ 10-2018-0115113

(51) Int. Cl.
*C12P 19/02* (2006.01)
*C12N 1/20* (2006.01)
*C12N 9/88* (2006.01)
*C12R 1/19* (2006.01)
*C12R 1/28* (2006.01)

(52) U.S. Cl.
CPC .............. *C12P 19/02* (2013.01); *C12N 1/20* (2013.01); *C12N 9/88* (2013.01); *C12R 2001/19* (2021.05); *C12R 2001/28* (2021.05); *C12Y 401/0204* (2013.01)

(58) Field of Classification Search
None
See application file for complete search history.

(56) References Cited

U.S. PATENT DOCUMENTS

| 2002/0159976 A1* | 10/2002 | Glenn ................. C07K 14/335 424/93.2 |
| 2020/0165639 A1* | 5/2020 | Zanghellini ............. C12P 19/02 |
| 2022/0002770 A1* | 1/2022 | Lee ........................ C12N 15/70 |

FOREIGN PATENT DOCUMENTS

| EP | 3211078 A1 | 8/2017 |
| EP | 3798311 A1 | 3/2021 |
| KR | 10-0964091 B1 | 6/2010 |
| KR | 10-1368731 B1 | 3/2014 |
| KR | 10-2015-0025703 A | 3/2015 |
| KR | 10-20150081823 A | 7/2015 |
| KR | 10-2015-0025703 A | 7/2016 |
| KR | 10-1638024 B1 | 7/2016 |
| KR | 10-20180111678 A | 10/2018 |
| WO | WO 2006/058092 A2 | 6/2006 |
| WO | WO 2020/010260 A1 | 1/2020 |

OTHER PUBLICATIONS

U.S. Appl. No. 62/693,681, Abstract, Specification, Claims and Drawings, filed Jul. 3, 2018 (Year: 2018).*
Zigby et al. (Eur. J. Biochem. vol. 267, pp. 1868-1868, 2000).*
International Search Report and Written Opinion of PCT/KR2019/010734 dated Nov. 29, 2019 together with the English translation of the international search report (total of 11 pages).
Brinkkotter, A. et al, "Two class II $_D$-tagatose-bisphosphate aldolases from enteric bacteria", Arch Microbiol, 2002, vol. 177, pp. 410-419; DOI 10.1007/s00203-002-0406-6.
NCBI, GenBank accession No. WP_094396757.1, tagatose-bisphosphate aldolase [Thermoanaerobacterium thermosaccharolyticum] Aug. 16, 2017.
NCBI, GenBank accession No. KTF17300.1, tagatose-bisphosphate aldolase [*Pseudoalteromonas* sp. H103] Dec. 17, 2015.
Extended European Search report of the EP application No. 19867046.5 dated Oct. 12, 2021.
DATABASE UniProt [Online]; Oct. 25, 2017, "D-tagatose-bisphosphate aldolase class II accessory protein", XP055846422; Database accession No. AOA223HVJ3.

* cited by examiner

*Primary Examiner* — Richard G Hutson
(74) *Attorney, Agent, or Firm* — Squire Patton Boggs (US) LLP

(57) ABSTRACT

Provided are a novel fructose-C4-epimerase and a method of producing tagatose using the same.

5 Claims, 3 Drawing Sheets

Specification includes a Sequence Listing.

FRUCTOSE-C4-EPIMERASE AND METHOD OF PRODUCING TAGATOSE USING THE SAME

This application includes an electronically submitted sequence listing in .txt format. The .txt file contains a sequence listing entitled "059520_00021_ST25.txt" created on Mar. 26, 2021 and is 12 KB in size. The sequence listing contained in this .txt file is part of the specification and is hereby incorporated by reference herein in its entirety.

TECHNICAL FIELD

The present disclosure relates to a novel fructose-C4-epimerase and a method of producing tagatose using the same.

BACKGROUND ART

Tagatose is a natural sweetener, which is present in a small amount in foods, such as milk, cheese, and cacao, and sweet fruits, such as apples and tangerines. Although tagatose has an energy value of 1.5 kcal/g, which is about one third of that of sucrose, and a glycemic index (GI) of 3, which is about 5% of that of sucrose, physical properties and taste of tagatose are similar to those of sucrose and tagatose has various functions beneficial to health. Therefore, tagatose may be used as a sugar substitute satisfying both health and taste.

Tagatose has been produced using galactose as a main raw material by a method well known or commonly used in the art, for example, a chemical method (catalytic reaction) and a biological method (isomerizing enzyme reaction) (International Patent Publication No. WO2006/058092, and Korean Patent Nos. 10-0964091 and 10-1368731). However, it is difficult to stably supply lactose, which has been used as a raw material of galactose used a main ingredient of tagatose in conventional production methods, because the price of lactose fluctuates in accordance with production, demand, and supply of raw milk and lactose. Therefore, there is a need to develop methods of producing tagatose using common sugars (sucrose, glucose, fructose, and the like) as a raw material.

DESCRIPTION OF EMBODIMENTS

Technical Problem

As a result of intensive researches to develop enzymes having activity to convert fructose into tagatose, the present inventors have found that tagatose-bisphosphate aldolase has fructose-C4-epimerase activity to convert fructose into tagatose, thereby completing the present disclosure.

Solution to Problem

An object of the present disclosure is to provide a composition for producing tagatose including at least one of: tagatose-bisphosphate aldolase; a microorganism expressing the same; and cultures of the microorganism.

Another object of the present disclosure is to provide a microorganism including at least one of the tagatose-bisphosphate aldolase, a polynucleotide encoding the same, and an expression vector including the polynucleotide.

Still another object of the present disclosure is to provide a method of producing tagatose including converting fructose into tagatose by contacting the composition with fructose.

Still another object of the present disclosure is to provide a use of the tagatose-bisphosphate aldolase as a fructose-C4-epimerase.

Advantageous Effects of Disclosure

Tagatose-bisphosphate aldolase that is the fructose-C4-epimerase according to the present disclosure is economically feasible due to excellent heat resistance enabling industrial production of tagatose and the ability to convert fructose, as a common sugar, into tagatose.

BEST MODE

Figure 1:
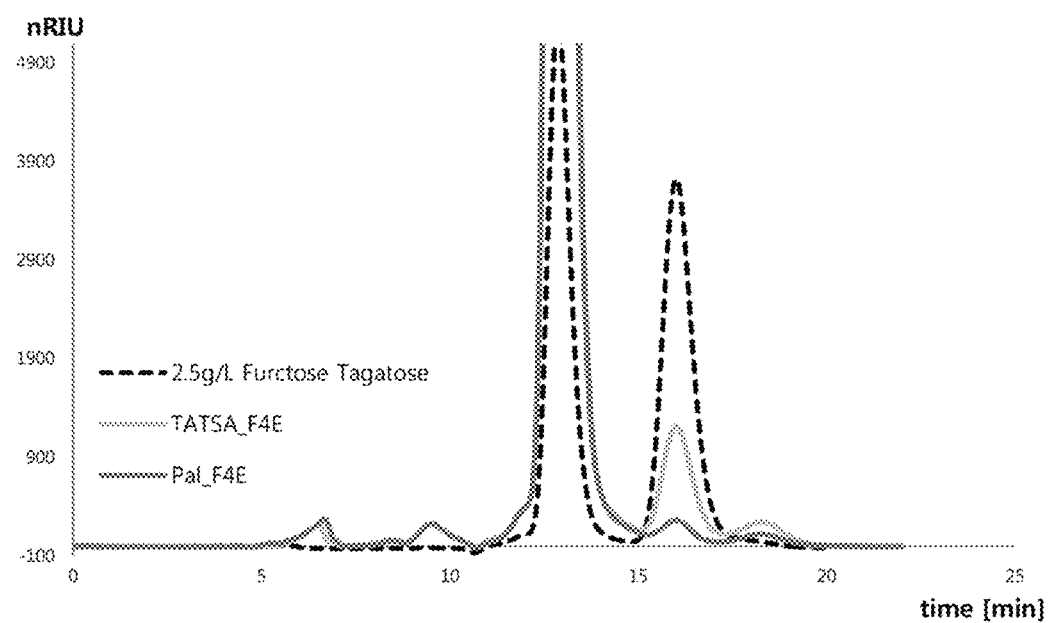
FIG. 1 is a high-performance liquid chromatography (HPLC) graph illustrating fructose-C4-epimerase activity of CJ_TATSA_F4E and CJ_Pal_F4E, as tagatose-bisphosphate aldolase.

Hereinafter, the present disclosure will be described in detail. Meanwhile, each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed description provided below.

Those skilled in the art will recognize or be able to ascertain, using no more than routine experimentation, many equivalents to specific embodiments of the present disclosure. Such equivalents are intended to be encompassed in the scope of the following present disclosure.

An aspect of the present disclosure to achieve the above objects provides a composition for producing tagatose including at least one of: tagatose-bisphosphate aldolase; a microorganism expressing the same; and cultures of the microorganism.

The present disclosure is characterized in that the tagatose-bisphosphate aldolase has fructose-C4-epimerase activity.

The fructose-C4-epimerase or a variant thereof has a characteristic of epimerizing D-fructose at C4 into D-tagatose. The fructose-C4-epimerase has tagatose-bisphosphate aldolase activity and produces glycerone phosphate and D-glyceraldehyde 3-phosphate using D-tagatose 1,6-bisphosphate as a substrate.

Meanwhile, although it has been reported that the tagatose-bisphosphate aldolase (EC4.1.2.40) produces glycerone phosphate and D-glyceraldehyde 3-phosphate using D-tagatose 1,6-bisphosphate as a substrate as shown in Reaction Scheme 1 below and involves in galactose metabolism, no research has been conducted on whether tagatose-bisphosphate aldolase has the activity to produce tagatose.

Reaction Scheme 1

D-tagatose 1,6-bisphosphate a glycerone phosphate+D-glyceraldehyde 3-phosphate

The present inventors have found that the tagatose-bisphosphate aldolase has the fructose-C4-epimerase activity. Therefore, according to an embodiment of the present disclosure, provided is a novel use of tagatose-bisphosphate aldolase as a fructose-C4-epimerase in the production of tagatose from fructose. In addition, according to another embodiment of the present disclosure, provided is a method of producing tagatose from fructose using tagatose-bisphosphate aldolase as a fructose-C4-epimerase.

In the present disclosure, any tagatose-bisphosphate aldolase capable of producing tagatose using fructose as a substrate may be used without limitation. Specifically, the tagatose-bisphosphate aldolase may have a conversion rate, from fructose, as a substrate, to tagatose, of 0.01% or greater, specifically 0.1% or greater, preferably 0.3% or greater (conversion rate=weight of tagatose/initial weight of fructose×100). More particularly, the conversion rate may be in the range of 0.01% to 40%, in the range of 0.1% to 30%, in the range of 0.3% to 25%, or in the range of 0.3% to 20%.

According to an embodiment, the tagatose-bisphosphate aldolase according to the present disclosure may be an enzyme having excellent heat resistance. Particularly, the tagatose-bisphosphate aldolase according to the present disclosure may exhibit an activity of 50% to 100%, 60% to 100%, 70% to 100%, or 75% to 100% of the maximum activity at a temperature of 30° C. to 70° C. More specifically, the tagatose-bisphosphate aldolase according to the present disclosure may exhibit the activity of 80% to 100% or 85% to 100% of the maximum activity at a temperature of 40° C. to 70° C., 40° C. to 65° C., 45° C. to 65° C., 45° C. to 60° C., or 45° C. to 55° C.

The tagatose-bisphosphate aldolase according to the present disclosure may be a thermophilic and thermotolerant microorganism-derived enzyme or a variant thereof, e.g., an enzyme derived from *Thermoanaerobacterium* sp. or a variant thereof, or an enzyme derived from *Pseudoalteromonas* sp. or a variant thereof, but is not limited thereto. Specifically, the tagatose-bisphosphate aldolase may be an enzyme derived from *Thermoanaerobacterium thermosaccharolyticum* or *Pseudoalteromonas* sp. H103 or a variant thereof.

The tagatose-bisphosphate aldolase according to the present disclosure may have an amino acid sequence having at least 85% identity with that of SEQ ID NO: 1 or 3. Specifically, the tagatose-bisphosphate aldolase may be a polypeptide having an amino acid sequence of SEQ ID NO: 1 or 3 or include a polypeptide having at least 80%, 90%, 95%, 97%, or 99% homology or identity with the amino acid sequence of SEQ ID NO: 1 or 3. In addition, it will be obvious to those skilled in the art that any polypeptide having an amino acid sequence including a deletion, a modification, a substitution, or an addition of one or several amino acids is within the scope of the present disclosure, as long as the polypeptide has an amino acid sequence retaining the homology or identity and an effect corresponding to the protein having an amino acid sequence of SEQ ID NO: 1 or 3 (i.e., the fructose-C4-epimerase activity to convert fructose into tagatose by epimerizing fructose at C4). In addition, any polypeptide having the fructose-C4-epimerase activity and encoded by a probe prepared from any known gene sequences, e.g., a polynucleotide hybridized with a sequence totally or partially complementary to the nucleotide sequence encoding the polypeptide under stringent conditions may be used, without limitation. In addition, the composition may include at least one tagatose-bisphosphate aldolase having an amino acid sequence retaining at least 85% identity with the amino acid sequence of SEQ ID NO: 1 or 3. Furthermore, the tagatose-bisphosphate aldolase having the amino acid sequence of SEQ ID NO: 1 may be encoded by a nucleotide sequence of SEQ ID NO: 2 and the tagatose-bisphosphate aldolase having the amino acid sequence of SEQ ID NO: 3 may be encoded by a nucleotide sequence of SEQ ID NO: 4, without being limited thereto.

Specifically, the tagatose-bisphosphate aldolase may have an amino acid sequence of SEQ ID NO: 1 or 3. The tagatose-bisphosphate aldolase according to the present disclosure may have an amino acid sequence of SEQ ID NO: 1 or 3 or an amino acid sequence having at least 50% homology or identity therewith, without being limited thereto. Specifically, the tagatose-bisphosphate aldolase according to the present disclosure may include a polypeptide having an amino acid sequence of SEQ ID NO: 1 or 3 or a polypeptide having at least 60%, 70%, 80%, 85%, 90%, 95%, 96%, 97%, 98%, or 99% homology or identity with the amino acid sequence of SEQ ID NO: 1 or 3. In addition, it will be obvious to those skilled in the art that any accessory protein having an amino acid sequence including a deletion, a modification, a substitution, or an addition of one or several amino acids is within the scope of the present disclosure, so long as the amino acid sequence retains the above-described homology or identity and an equivalent effect to that of the protein.

It is also obvious to those skilled in the art that any polynucleotide translated into the protein comprising the amino acid sequence of SEQ ID NO: 1 or 3 or a protein having homology or identity therewith by codon degeneracy is within the scope of the present disclosure. Alternately, any probe prepared from known gene sequences, e.g., a nucleotide sequence hybridized, under stringent conditions, with a sequence totally or partially complementary to the nucleotide sequence encoding a protein having the activity of the protein having the amino acid sequence set forth in SEQ ID NO: 1 or 3 may be used, without limitation. The term "stringent conditions" refers to conditions which permit specific hybridization between polynucleotides. Such conditions are disclosed in detail in known documents (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). For example, the stringent conditions may include performing hybridization between genes having a high homology or identity, a homology or identity of 80% or higher, 85% or higher, specifically 90% or higher, more specifically 95% or higher, even more specifically 97% or higher, and most specifically 99% or higher, without performing hybridization between genes having a homology or identity lower than the above homologies or identities, or performing washing once, specifically twice or three times, under conventional washing conditions for Southern hybridization of 60° C., 1×SSC, and 0.1% SDS, specifically at a salt concentration and a temperature of 60° C., 0.1×SSC, 0.1% SDS, and more specifically 68° C., 0.1×SSC, and 0.1% SDS.

In other words, although it is disclosed as 'a protein or polypeptide comprising an amino acid sequence set forth in a predetermined SEQ ID NO:', it will be obvious to those skilled in the art that any protein having an amino acid sequence including a deletion, a modification, a substitution, a conservative substitution, or an addition of one or several amino acids may also be used in the present disclosure as long as the protein has homologous or identical activity to that of the polypeptide having the amino acid sequence of the present disclosure. For example, it is obvious to those skilled in the art that any protein having an addition of a sequence not changing functions of the protein, a naturally occurring mutation or a silent mutation thereof, or a conservative substitution in the forward or reverse direction is not excluded as long as the protein has identical or homologous activity with that of the modified polypeptide, and any protein having such addition of a sequence or mutation may also be within the scope of the present disclosure.

The term "conservative substitution" refers to a substitution of one amino acid with another amino acid having a similar structural and/or chemical property. Such an amino acid substitution may generally occur based on similarity of polarity, charge, solubility, hydrophobicity, hydrophilicity, and/or amphipathic nature of a residue. For example, positively charged (basic) amino acids include arginine, lysine, and histidine; negatively charged (acidic) amino acids include glutamic acid and aspartic acid; aromatic amino acids include phenylalanine, tryptophan, and tyrosine, and hydrophobic amino acids include alanine, valine, isoleucine, leucine, methionine, phenylalanine, tyrosine, and tryptophan.

Hybridization requires that two polynucleotides have complementary sequences, although mismatch between bases is available according to the degree of stringency of hybridization. The term "complementary" is used to describe the relationship between nucleotide bases capable of hybridizing with each other. For example, with respect to DNA, adenosine is complementary to thymine, and cytosine is complementary to guanine. Thus, the present disclosure may include not only a substantially similar polynucleotide sequence but also an isolated polynucleotide fragment complementary to the entire sequence.

Specifically, the polynucleotide having homology or identity may be detected using the above-described conditions under hybridization conditions including a hybridization process using a Tm value of 55° C. Also, the Tm value may be, but is not limited to, 60° C., 63° C., or 65° C. and may be appropriately adjusted by those skilled in the art according to the purpose.

An appropriate degree of stringency for hybridization of polynucleotides may depend on a length of the polynucleotides and a degree of complementarity and parameters thereof are well known in the art (Sambrook et al., supra, 9.50-9.51, 11.7-11.8).

The "homology" or "identity" refers to a degree of relevance between two amino acid sequences or nucleotide sequences and may be shown as a percentage. The terms homology and identity may often be used interchangeably.

Sequence homology or identity of conserved polynucleotides or polypeptides may be determined by standard alignment algorithm and default gap penalties established by a program may be used together therewith. Substantially, homologous or identical sequences may hybridize to each other at least about 50%, 60%, 70%, 80%, or 90% of the entire sequence or the entire length under moderate or highly stringent conditions. In hybridized polynucleotides, polynucleotide containing degenerated codon instead of codon may also be considered.

The degree of homology, similarity, or identity between any two polynucleotide or polypeptide sequences may be determined using computer algorithms known in the art, e.g., "FASTA" program using default parameters (Pearson et al (1988) [Proc. Natl. Acad. Sci. USA 8: 2444]. Alternatively, Needleman-Wunsch algorithm (1970, J. Mol. Biol. 48: 443-453) performed in a Needleman program of The European Molecular Biology Open Software Suite (EMBOSS) package (Rice et al., 2000, Trends Genet. 16: 276-277) (version 5.0.0 or later) may be used to determine the same (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). Additionally, the homology, similarity, or identity may be determined using BLAST, from the National Center for Biotechnology Information database, or ClustalW.

The degree of homology, similarity, or identity between polynucleotides or polypeptides may be determined by comparing sequence information using a GAP computer program, e.g., a program introduced by Needleman et al., (1970), J Mol Biol. 48: 443 as disclosed in Smith and Waterman, Adv. Appl. Math (1981) 2:482. In brief, the GAP program defines similarity as the number of aligned symbols (i.e., nucleotides or amino acids) which are similar, divided by the total number of symbols in a shorter of two sequences. Default parameters for the GAP program may include: (1) a binary number system (containing a value of 1 for identities and 0 for non-identifies) and the weighted comparison matrix of Gribskov, et al., Nucl. Acids Res. 14: 6745 (1986) as described by Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps. Therefore, as used herein, the term "homology" or "identity" refers to relevance between sequences.

According to another aspect of the present disclosure, provided is a microorganism comprising at least one of the tagatose-bisphosphate aldolase, a polynucleotide encoding the same, and an expression vector including the polynucleotide.

As used herein, the term "polynucleotide" has an inclusive meaning including DNA or RNA molecules, and a nucleotide that is a basic structural unit in the polynucleotide may include not only a natural nucleotide but also an analogue in which a sugar or a base is modified (Scheit, Nucleotide Analogs, John Wiley, New York (1980); Uhlman and Peyman, Chemical Reviews, 90:543-584 (1990)).

The polynucleotide may be a polynucleotide encoding a polypeptide comprising an amino acid sequence having at least 85% identity with SEQ ID NO: 1 or 3 according to the present disclosure or a polynucleotide encoding a polypeptide having fructose-4-epimerase activity as well as having at least 80%, 85%, 90%, 95%, 96%, 97%, 98%, or 99% homology with the tagatose-bisphosphate aldolase according to the present disclosure. Specifically, for example, the polynucleotide encoding tagatose-bisphosphate aldolase comprising an amino acid sequence having at least 85% identity with SEQ ID NO: 1 or 3 may be a polynucleotide having at least 80%, 85%, 90%, 95%, 96%, 97%, 98%, 99%, or 100% homology or identity with the nucleotide sequence of SEQ ID NO: 2 or 4. In addition, as described above, it is obvious that the polynucleotide according to the present disclosure also may include a polynucleotide that is translated into the tagatose-bisphosphate aldolase according to the present disclosure by codon degeneracy and a polynucleotide that is hybridized with a polynucleotide consisting of a nucleotide sequence complementary to SEQ ID NO: 2 or 4 under stringent conditions and has the fructose-C4-epimerase activity according to the present disclosure.

The microorganism expressing tagatose-bisphosphate aldolase available in the present disclosure may be a microorganism comprising at least one of the polypeptide, a polynucleotide encoding the polypeptide, and a recombinant vector including the polynucleotide. The vector may be in a form operably linked to the polynucleotide according to the present disclosure. As used herein, the term "operably linked" refers to a linkage of a nucleotide expression regulatory sequence to a nucleotide sequence encoding a target protein to perform general functions thereof and an operable linkage may affect the expression of the encoding nucleotide sequence. An operable linkage with a vector may be formed by a genetic recombination technique known in the art, and site-specific DNA cleavage and ligation may be performed using a restriction enzyme, a ligase, and the like, known in the art.

As used herein, the term "vector" refers to a mediator for cloning and/or transferring nucleotides to an organism, e.g., a host cell. A vector may be a replicon that enables replication of a DNA fragment bound by another DNA fragment. As used herein, the term "replicon" refers to a genetic unit acting as a self-replicating unit for DNA replication in vivo, i.e., being replicable by self-regulation (e.g., plasmid, phage, cosmid, chromosome, and virus). The term "vector", as used herein, may include viral and non-viral mediators for introducing nucleotides into an organism, e.g., a host cell in vitro, ex vivo, or in vivo, and also may include a mini-spherical DNA, a transposon such as Sleeping Beauty (Izsvak et al., J. Mol. Biol. 302:93-102 (2000)), or an artificial chromosome. Examples of common vectors may include plasmid, cosmid, virus, and bacteriophage in a natural or recombinant form. For example, pWE15, M13, MBL3, MBL4, IXII, ASHII, APII, t10, t11, Charon4A, and Charon21A may be used as a phage vector or cosmid vector, and pBR-based, pUC-based, pBluescriptII-based, pGEM-based, pTZ-based, pCL-based, and pET-based vectors may be used as a plasmid vector. The vector available according to the present disclosure is not particularly limited and any known recombinant rectors may also be used. In addition, the vector may be a recombinant vector further including various antibiotic resistance genes. As used herein, the term "antibiotic resistance gene" refers to a gene having resistance to antibiotics, and the cells having this gene may survive even in an environment treated with the antibiotics. Therefore, the antibiotic resistance gene may be effectively used as a selective marker for a large-scale production of plasmids in *E. coli*. In the present disclosure, the antibiotic resistance gene is not a factor that significantly affects the expression efficiency according to an optimal combination of vectors which is core technology of the present disclosure, and thus any common antibiotic resistance gene may be used as a selective marker without limitation. For example, genes resistant to ampicilin, tetracyclin, kanamycin, chloroamphenicol, streptomycin, or neomycin may be used.

The microorganism expressing tagatose-bisphosphate aldolase available in the present disclosure may be prepared by a method of introducing a vector including a polynucleotide encoding the enzyme into a host cell. A method of transforming the vector may include any method capable of introducing polynucleotides into cells and may be performed by selecting an appropriate standard technique known in the art. For example, electroporation, calcium phosphate co-precipitation, retroviral infection, microinjection, DEAE-dextran, cationic liposome, and heat shock method may be used, without being limited thereto. According to an embodiment, the microorganism expressing tagatose-bisphosphate aldolase may be a microorganism for producing tagatose including tagatose-bisphosphate aldolase comprising an amino acid sequence having at least 85% identity with SEQ ID NO: 1 or 3 or a polynucleotide encoding the same.

The transformed gene may include either in a form inserted into the chromosome of a host cell or in a form located outside the chromosome, as long as the gene is expressed in the host cell. In addition, the gene includes DNA and RNA as a polynucleotide encoding a polypeptide and any gene that may be introduced into a host cell and expressed in the host cell may be used without limitation. For example, the gene may be introduced into the host cell in the form of an expression cassette that is a polynucleotide construct including all of the essential elements required for self-expression. The expression cassette may generally include a promoter operably linked to the gene, a transcription termination signal, a ribosome-binding domain, and a translation termination signal. The expression cassette may be in the form of a recombinant vector capable of self-replication. In addition, the gene may be introduced into the host cell by itself or in the form of a polynucleotide construct and operably linked to a sequence required for the expression in the host cell.

The microorganism according to the present disclosure may include any of the prokaryotic and eukaryotic microorganisms which are capable of producing tagatose-bisphosphate aldolase according to the present disclosure comprising the polynucleotide or the recombinant vector according to the present disclosure. Examples of the microorganism may include, but are not limited to, microbial strains belonging to the genus of *Escherichia*, the genus of *Erwinia*, the genus of *Serratia*, the genus of *Providencia*, the genus of Corynebacteria, and the genus of Brevibacteria, specifically, *E. coli*, or *Corynebacterium glutamicum*.

The cultures of the microorganism according to the present disclosure may be prepared by culturing the microorganism according to the preset disclosure in a culture medium.

As used herein, the term "culturing" refers to growing the microorganism in an appropriately adjusted environment. In the present disclosure, the culturing may be performed in appropriate media and culturing conditions well-known in the art. The culturing may be easily adjusted by one of ordinary skill in the art according to a microbial strain being selected. The culturing of the microorganism may be performed continuously in a batch process, a continuous process, a fed-batch process, etc. known in the art, without being limited thereto. In particular, with respect to the culturing conditions, the pH may be adjusted to a suitable pH (e.g., pH 5 to 9, specifically pH 7 to 9), by using an appropriate basic compound (e.g., sodium hydroxide, potassium hydroxide, or ammonia) or an acidic compound (e.g., phosphoric acid or sulfuric acid). Additionally, during the culturing, an antifoaming agent, such as fatty acid polyglycol ester, may be used to prevent foam generation. In addition, an aerobic condition of the culture may be maintained by introducing oxygen or an oxygen-containing gas to the cultures, and an anaerobic and microaerobic states of the culture may be maintained by introducing nitrogen, hydrogen, or carbon dioxide gas to the culture without the injection of other gases. The culturing temperature may be maintained in the range of 25° C. to 40° C., and specifically 30° C. to 37° C., without being limited thereto. Additionally, the culturing may be continued until a desired yield of a desired substance is obtained, and specifically for about 0.5 hours to 60 hours, without being limited thereto. In addition, as the carbon sources to be used in the culture medium, sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid) may be used alone or in combination, without being limited thereto. As the nitrogen sources to be used in the culture medium, nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), and the like may be used alone or in combination, without being limited thereto. As the phosphorus sources to be used in the culture medium, potassium dihydrogen phosphate, dipotassium hydrogen phosphate, sodium-containing salts corresponding thereto, and the like may be used alone or in combination, without being limited thereto. Additionally, metal salts (e.g., magnesium sulfate or iron sulfate), amino acids, vitamins, and the like which are essential growth-promoting materials, may be contained in the culture medium.

The composition for producing tagatose according to the present disclosure may include further fructose.

The composition for producing tagatose according to the present disclosure includes tagatose-bisphosphate aldolase having fructose-C4-epimerase activity directly converting fructose into tagatose, a microorganism expressing the same, or cultures of the microorganism, and the tagatose-bisphosphate aldolase or a variant thereof may produce tagatose using fructose, as a substrate.

The composition for producing tagatose according to the present disclosure may include further any suitable excipient commonly used in compositions for producing tagatose. Examples of the excipient may be, but are not limited to, a preservative, a humectant, a dispersant, a suspension, a buffer solution, a stabilizer, or an isotonic agent.

The composition for producing tagatose according to the present disclosure may include further a metal. According to an embodiment of the present disclosure, the metal may be a metal having a divalent cation. Particularly, the metal according to the present disclosure may be nickel (Ni), magnesium (Mg), or manganese (Mn). More particularly, the metal according to the present disclosure may be a metal ion or a metal salt. More particularly, the metal salt may be $MgSO_4$, $NiSO_4$, $NiCl_2$, $MgCl_2$, $MnCl_2$, or $MnSO_4$.

According to another aspect of the present disclosure, provided is a method of preparing tagatose including converting fructose into tagatose by contacting the composition with fructose.

The tagatose-bisphosphate aldolase is as described above.

According to an embodiment, the contacting of the present disclosure may be performed at a pH 5.0 to 9.0 at a temperature of 30° C. to 80° C. and/or for 0.5 hours to 48 hours.

Specifically, the contacting according to the present disclosure may be performed at a pH of 6.0 to 9.0 or pH 7.0 to 9.0. In addition, the contacting according to the present disclosure may be performed at a temperature of 30° C. to 80° C., 35° C. to 80° C., 40° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50° C. to 65° C., 55° C. to 65° C., 30° C. to 60° C., 35° C. to 60° C., 40° C. to 60° C., 45° C. to 60° C., 40° C. to 55° C., or 45° C. to 55° C. In addition, the contacting of the present disclosure may be performed for 0.5 hours to 36 hours, 0.5 hours to 24 hours, 0.5 hours to 12 hours, 0.5 hours to 6 hours, 1 hour to 48 hours, 1 hour to 36 hours, 1 hour to 24 hours, 1 hour to 12 hours, 1 hour to 6 hours, 3 hours to 48 hours, 3 hours to 36 hours, 3 hours to 24 hours, 3 hours to 12 hours, 3 hours to 6 hours, 6 hours to 48 hours, 6 hours to 36 hours, 6 hours to 24 hours, 6 hours to 12 hours, 12 hours to 48 hours, 12 hours to 36 hours, 12 hours to 24 hours, 18 hours to 48 hours, 18 hours to 36 hours, or 18 hours to 30 hours.

According to an embodiment, the contacting of the present disclosure may be performed in the presence of a metal. The metal available therefor is as described above.

The preparation method according to the present disclosure may include further separating and/or purifying the prepared tagatose. The separating and/or purifying may be performed using any method commonly used in the art, for example, but not limited to, dialysis, precipitation, adsorption, electrophoresis, ion exchange chromatography, and fractional crystallization. The purifying may be implemented by using the methods alone or in combination thereof.

In addition, the preparation method according to the present disclosure may include further decoloring and/or desalting the prepared tagatose before or after the separating and/or purifying. By performing decoloring and/or desalting, tagatose having higher quality may be obtained.

According to another embodiment, the preparation method of the present disclosure may include further crystallizing tagatose after the converting, the separating and/or purifying, or the decoloring and/or desalting. The crystallization of tagatose may be performed by using any crystallization method commonly used in the art. For example, cooling crystallization may be used for crystallizing tagatose.

According to another embodiment, the preparation method of the present disclosure may include further concentrating tagatose before the crystallizing. The concentrating may increase a crystallization efficiency.

According to another embodiment, the preparation method of the present disclosure may include further contacting unreacted fructose with the enzyme according to the present disclosure, the microorganism expressing the enzyme, or the cultures of the microorganism after the separation and/or purification of tagatose; reusing a solution from which crystals are separated in the separating and/or purifying of tagatose after the crystallizing; or any combination thereof.

According to another aspect of the present disclosure, provided is a use of tagatose-bisphosphate aldolase as a fructose-C4-epimerase.

The tagatose-bisphosphate aldolase, homology, and identity are as described above.

MODE OF DISCLOSURE

Hereinafter, the present disclosure will be described in more detail with reference to the following examples and experimental examples. However, these examples and experimental examples are for illustrative purposes only, and the present disclosure is not intended to be limited by these examples and experimental examples.

Example 1: Preparation of Recombinant Expression Vector Including Gene of Tagatose-Bisphosphate Aldolase and Transformed Microorganism In order to discover a novel thermostable fructose-C4-epimerase, gene information similar to that of tagatose-bisphosphate aldolase derived from *Thermoanaerobacterium thermosaccharolyticum* or *Pseudoalteromonas* sp. H103 was obtained and a vector expressed by *Escherichia coli* (*E. coli*) and a transformed microorganism were prepared.

Specifically, gene sequences similar to that of tagatose-bisphosphate aldolase were selected from the gene sequence of *Thermoanaerobacterium thermosaccharolyticum* or *Pseudoalteromonas* sp. H103 registered in The Kyoto Encyclopedia of Genes and Genomes (KEGG) and The National Center for Biotechnology Information (NCBI), and recombinant vectors of pBT7-C-His-CJ_TATSA_F4E and pBT7-C-His-CJ_Pal_F4E including a nucleotide sequence of the enzyme and expressible in *E. coli* were prepared using a pBT7-C-His vector (Bioneer Corporation, Korea) based on information on amino acid sequences (SEQ ID NOS: 1 and 3) and nucleotide sequences (SEQ ID NOS: 2 and 4) of the two microorganisms.

*E. coli* BL21(DE3) was transformed by heat shock transformation (Sambrook and Russell: Molecular cloning, 2001) using each recombinant vector prepared as described above. Specifically, 1 µL of each of the prepared recombinant plasmid vector DNAs was added to a 1.5 mL tube and 50 µL of *E. coli* BL21(DE3) competent cells (Novagen®, Germany) were added thereto, followed by incubation on ice for 30 minutes or more, and then heat-treatment in a water bath at 42° C. for 30 seconds. The *E. coli* was inoculated onto 500 µL of a Luria-Bertani (LB) medium thereto and cultured in a shaking incubator at 37° C. for 1 hour, and then inoculated onto a culture tube including 5 mL of an LB liquid medium supplemented with ampicillin as an antibiotic and cultured in a shaking incubator at 37° C. The transformed *E. coli* was stored frozen in 50% glycerol. The transformed strains were named *E. coli* BL21(DE3)/CJ_TATSA_F4E and *E. coli* BL21(DE3)/CJ_Pal_F4E, respectively.

Example 2: Preparation and Purification of Recombinant Enzyme

To prepare a recombinant enzyme, the transformed strains prepared in Example 1 above (i.e., *E. coli* BL21(DE3)/CJ_TATSA_F4E and *E. coli* BL21(DE3)/CJ_Pal_F4E) were inoculated onto a culture tube including 5 mL of an LB liquid medium supplemented with ampicillin as an antibiotic and seed culture thereof was performed in a shaking incubator at 37° C. at 600 nm until an absorbance reached 2.0. A culture solution obtained from the seed culture was inoculated onto a flask including a liquid medium supplemented with LB and lactose, as a protein expression regulatory factor, to perform main culture. The seed culture and the main culture were performed at a stirring rate of 180 rpm and at 37° C. Subsequently, the culture solution was centrifuged at 8,000 rpm at 4° C. for 20 minutes and strains were collected therefrom. The collected strains were washed twice with a 50 mM Tris-HCl buffer solution (pH 8.0) and resuspended in a 50 mM $NaH_2PO_4$ buffer solution (pH 8.0) including 10 mM imidazole and 300 mM NaCl. The resuspended strains were lysed with a sonicator and centrifuged at 13,000 rpm at 4° C. for 20 minutes, and only a supernatant was obtained therefrom. The supernatant was purified by histidine tag (His-tag) affinity chromatography, and non-specific binding proteins were removed therefrom by flowing a 50 mM $NaH_2PO_4$ buffer solution (pH 8.0) containing 20 mM imidazole and 300 mM NaCl in an amount of 10 times as much as that of a filler. Thereafter, the resultant was eluted and purified by further flowing the 50 mM $NaH_2PO_4$ buffer solution (pH 8.0) including 250 mM imidazole and 300 mM NaCl, and then subjected to dialysis using a 50 mM Tris-HCl buffer solution (pH 8.0) to obtain purified enzymes CJ_TATSA_F4E and CJ_Pal_F4E, for analysis of enzyme characteristics.

Example 3: Conversion from Fructose into Tagatose and Identification of Activity In order to measure the fructose-C4-epimerase activity of the recombinant enzymes, CJ_TATSA_F4E and CJ_Pal_F4E, according to the present disclosure prepared in Example 2 above, 50 mM Tris-HCl (pH 8.0), 1 mM $NiSO_4$, and 20 mg/mL of each of CJ_TATSA_F4E and CJ_Pal_F4E were added to 30 wt % of fructose and the mixtures were reacted at 55° C. for 10 hours.

Quantitative analysis was performed for fructose and tagatose, as a product, by HPLC after the reaction was terminated. HPLC was performed using a Shodex Sugar SP0810 column kept at 80° C. with water, as a mobile phase, at a flow rate of 1 mL/min (FIG. 1).

As a result of the experiment, conversion rates from fructose into tagatose by enzymatic reactions of CJ_TATSA_F4E and CJ_Pal_F4E were identified as 9.51% and 2.39%, respectively.

| | Conversion rate from fructose into tagatose |
|---|---|
| CJ_TATSA_F4E | 9.51% |
| CJ_Pal_F4E | 2.39% |

Example 4: Identification of Activity of Recombinant Enzyme According to Temperature In order to investigate influence of temperature on fructose-C4-epimerase activity of the enzymes CJ_TATSA_F4E and CJ_Pal_F4E prepared in Example 2 above, 10 mg/mL of each of CJ_TATSA_F4E and CJ_Pal_F4E was added to a 50 mM Tris HCl buffer solution (pH 8.0) supplemented with 10 wt % fructose, and each mixture was reacted at various temperatures, e.g., at 45° C., 50° C., 55° C., 60° C., and 65° C. for 10 hours. Quantitative analysis was performed for tagatose by HPLC after the reaction was terminated.

Figure 2A:
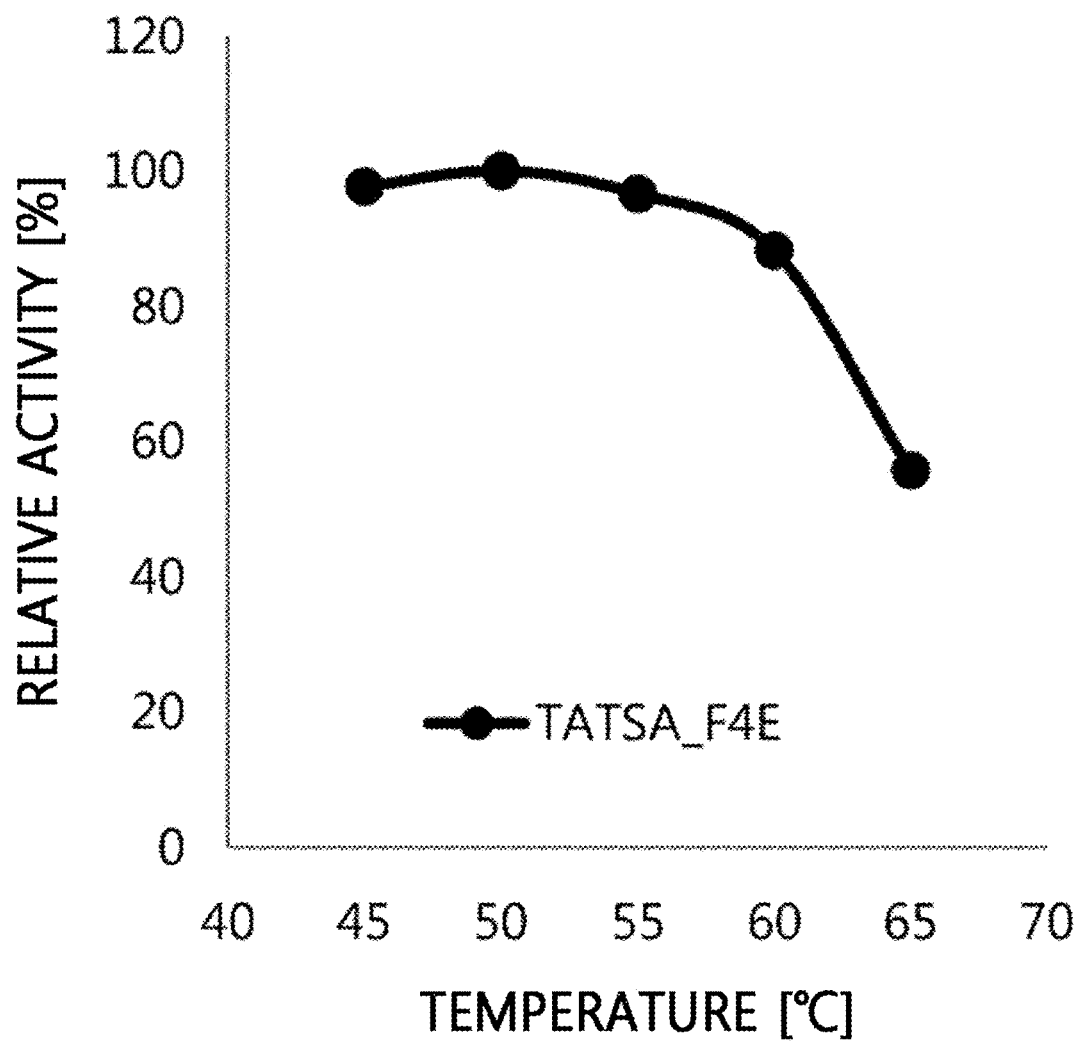
FIG. 2A is a graph illustrating fructose-C4-epimerase activity of CJ_TATSA_F4E, as tagatose-bisphosphate aldolase with respect to temperature change.
Figure 2B:
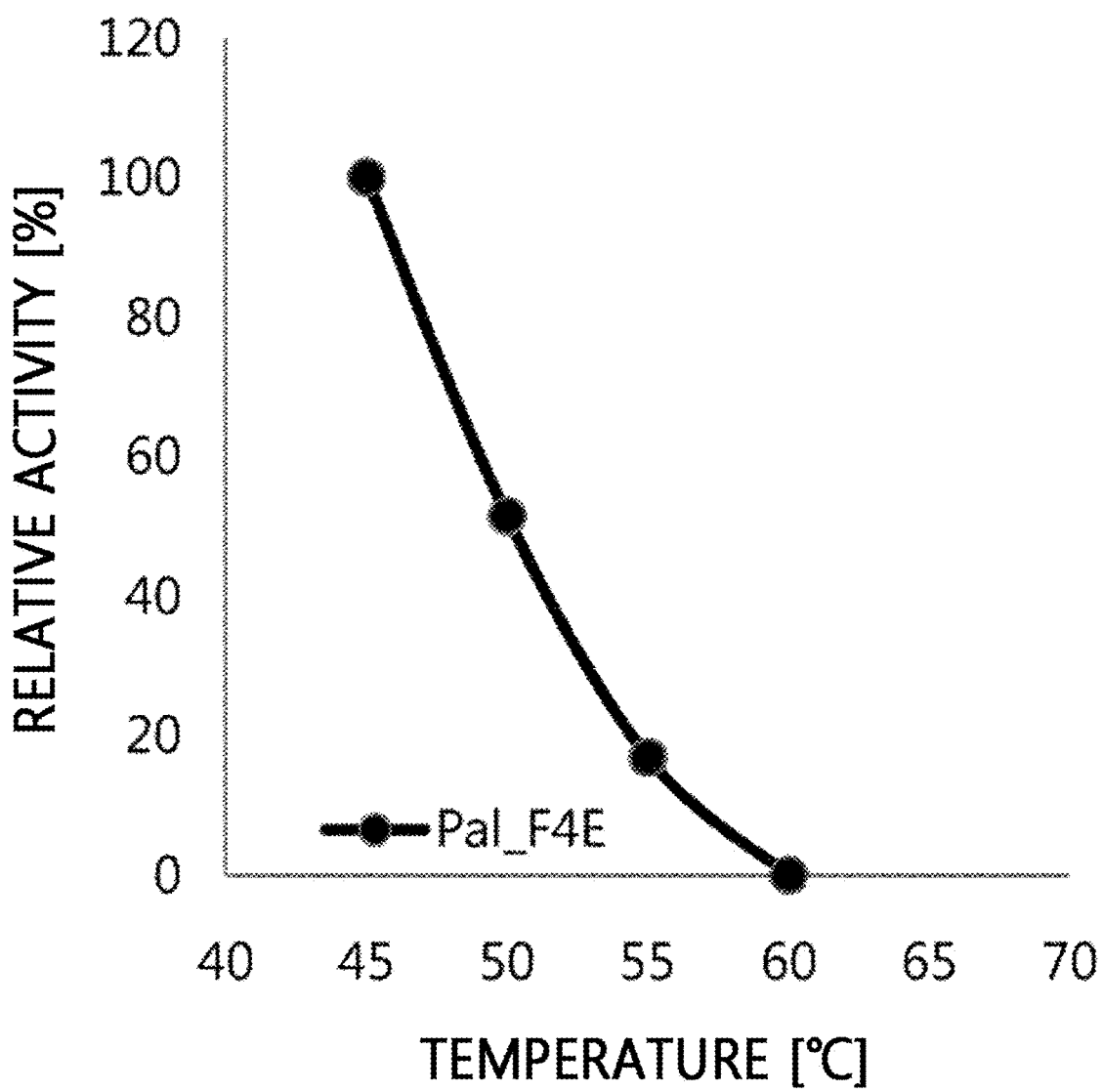
FIG. 2B is a graph illustrating fructose-C4-epimerase activity of CJ_Pal_F4E, as tagatose-bisphosphate aldolase with respect to temperature change.

As a result of the experiment, CJ_TATSA_F4E had a maximum activity at 50° C., 80% or more of the maximum activity was maintained at a temperature of 45° C. to 60° C., and 50% or more of the maximum activity was maintained in the entire temperature range (FIG. 2A). In addition, CJ_Pal_F4E had a maximum activity at 45° C. (FIG. 2B).

The above description of the present disclosure is provided for the purpose of illustration, and it would be understood by those skilled in the art that various changes and modifications may be made without changing technical conception and essential features of the present disclosure. Therefore, it is clear that the above-described embodiments are illustrative in all aspects and do not limit the present disclosure. Therefore, the scope of the disclosure is defined not by the detailed description, but by the claims and their equivalents, and all variations within the scope of the claims and their equivalents are to be construed as being included in the disclosure.

The invention claimed is:

1. A method of producing tagatose, the method comprising converting fructose into tagatose by contacting fructose with a tagatose-bisphosphate aldolase consisting of the amino acid sequence of SEQ ID NO: 3 or a microorganism which expresses the tagatose-bisphosphate aldolase consisting of the amino acid sequence of SEQ ID NO: 3.

2. The method according to claim 1, wherein the contacting is performed at a temperature of 45° C. to 65° C.

3. The method according to claim 1, wherein the contacting is performed at a pH of 5 to 9.

4. The method according to claim 1, wherein the contacting is performed in the presence of at least: a metal, a metal ion or a metal salt.

5. The method according to claim 4, wherein the metal, the metal ion and the metal salt are selected from the group consisting of nickel (Ni), magnesium (Mg), and manganese (Mn), and respective ions and salts thereof.

* * * * *

SEQUENCE LISTING

<160> NUMBER OF SEQ ID NOS: 4

<210> SEQ ID NO 1
<211> LENGTH: 434
<212> TYPE: PRT
<213> ORGANISM: Artificial Sequence
<220> FEATURE:
<223> OTHER INFORMATION: Synthetic: CJ_TATSA_F4E

<400> SEQUENCE: 1

```
Met Ala Lys Glu His Pro Leu Lys Glu Leu Val Asn Lys Gln Lys Ser
1               5                   10                  15

Gly Ile Ser Glu Gly Ile Val Ser Ile Cys Ser Ser Asn Glu Phe Val
            20                  25                  30

Ile Glu Ala Ser Met Glu Arg Ala Leu Thr Asn Gly Asp Tyr Val Leu
        35                  40                  45

Ile Glu Ser Thr Ala Asn Gln Val Asn Gln Tyr Gly Gly Tyr Ile Gly
    50                  55                  60

Met Thr Pro Ile Glu Phe Lys Lys Phe Val Phe Ser Ile Ala Lys Lys
65                  70                  75                  80

Val Asp Phe Pro Leu Asp Lys Leu Ile Leu Gly Gly Asp His Leu Gly
                85                  90                  95

Pro Leu Ile Trp Lys Asn Glu Ser Ser Asn Leu Ala Leu Ala Lys Ala
            100                 105                 110

Ser Glu Leu Ile Lys Glu Tyr Val Leu Ala Gly Tyr Thr Lys Ile His
        115                 120                 125

Ile Asp Thr Ser Met Arg Leu Lys Asp Asp Thr Asp Phe Asn Thr Glu
    130                 135                 140

Ile Ile Ala Gln Arg Ser Ala Val Leu Leu Lys Ala Ala Glu Asn Ala
145                 150                 155                 160

Tyr Met Glu Leu Asn Lys Asn Lys Asn Val Leu His Pro Val Tyr
                165                 170                 175

Val Ile Gly Ser Glu Val Pro Ile Pro Gly Gly Ser Gln Gly Ser Asp
            180                 185                 190

Glu Ser Leu Gln Ile Thr Asp Ala Lys Asp Phe Glu Asn Thr Val Glu
        195                 200                 205

Ile Phe Lys Asp Val Phe Ser Lys Tyr Gly Leu Ile Asn Glu Trp Glu
    210                 215                 220

Asn Ile Val Ala Phe Val Gln Pro Gly Val Glu Phe Gly Asn Asp
225                 230                 235                 240

Phe Val His Glu Tyr Lys Arg Asp Glu Ala Lys Glu Leu Thr Asp Ala
                245                 250                 255

Leu Lys Asn Tyr Lys Thr Phe Val Phe Glu Gly His Ser Thr Asp Tyr
            260                 265                 270

Gln Thr Arg Glu Ser Leu Lys Gln Met Val Glu Asp Gly Ile Ala Ile
        275                 280                 285

Leu Lys Val Gly Pro Ala Leu Thr Phe Ala Leu Arg Glu Ala Leu Ile
    290                 295                 300

Ala Leu Asn Asn Ile Glu Asn Glu Leu Leu Asn Asn Val Asp Ser Ile
305                 310                 315                 320

Lys Leu Ser Asn Phe Thr Asn Val Leu Val Ser Glu Met Ile Asn Asn
                325                 330                 335

Pro Glu His Trp Lys Asn His Tyr Phe Gly Asp Asp Ala Arg Lys Lys
            340                 345                 350

Phe Leu Cys Lys Tyr Ser Tyr Ser Asp Arg Cys Arg Tyr Tyr Leu Pro
```

```
              355                 360                 365
Thr Arg Asn Val Lys Asn Ser Leu Asn Leu Leu Ile Arg Asn Leu Glu
        370                 375                 380

Asn Val Lys Ile Pro Met Thr Leu Ile Ser Gln Phe Met Pro Leu Gln
385                 390                 395                 400

Tyr Asp Asn Ile Arg Arg Gly Leu Ile Lys Asn Glu Pro Ile Ser Leu
                    405                 410                 415

Ile Lys Asn Ala Ile Met Asn Arg Leu Asn Asp Tyr Tyr Tyr Ala Ile
            420                 425                 430

Lys Pro

<210> SEQ ID NO 2
<211> LENGTH: 1305
<212> TYPE: DNA
<213> ORGANISM: Artificial Sequence
<220> FEATURE:
<223> OTHER INFORMATION: Synthetic: CJ_TATSA_F4E

<400> SEQUENCE: 2
atggctaaag aacatccatt aaaggaatta gtaaataaac aaaaaagtgg tatatccgag      60
ggtatagttt ctatttgtag ttcaaatgaa tttgttattg aagcatctat ggagcgtgca     120
ttaacaaatg gtgattatgt tttaattgaa tcaacagcaa atcaggtgaa tcaatatggt     180
ggatatattg gtatgacacc tattgagttt aaaaaatttg tattttcaat agctaaaaaa     240
gtagattttc cattagataa attgattctt ggtggggatc atttaggccc attaatatgg     300
aaaaatgaat ctagtaattt ggcgttagca aaagcatccg agcttattaa agaatatgta     360
ttagccggat atactaaaat tcatatagac actagtatgc ggctaaaaga tgatactgat     420
tttaatacag aaattattgc tcaaagaagt gcagtattgt taaaggcagc ggaaaatgca     480
tatatggaat tgaataaaaa taataaaaat gttttacatc ctgtctatgt tataggaagt     540
gaagtcccaa tacctggggg cagccaaggc agtgatgaat cgctcccaaat tactgatgct     600 aaggattttg aaaatacagt tgaaatattt aaagatgttt tttcaaaata tggattaatt     660
aatgagtggg aaaacatagt agcatttgtt gttcaaccag gagttgagtt tggaaatgat     720
tttgtacatg aatataaacg tgatgaagca aaagaattaa cagatgcact taaaaattat     780
aaaacatttg tttttgaagg acattctact gattatcaaa cacgtgaatc attaaaacaa     840
atggtggaag atggcattgc aatttttaaaa gttggacctg cattaacatt tgcactacgt     900
gaagccttaa tagcactaaa taatatagaa aatgagttgc ttaataatgt agatagtata     960
aaattatcaa attttactaa tgtactcgta agtgaaatga tcaataaccc cgaacattgg    1020
aaaaatcatt attttggtga tgatgcaagg aaaaagtttc tatgtaaata tagttattcg    1080
gatagatgta ggtactattt accaactaga aatgtaaaaa actcattaaa tcttcttatt    1140
agaaatctag aaaatgtgaa ataccaatg acattaataa gtcaatttat gcctttgcaa    1200
tatgataata ttagaagagg actcataaaa aatgaaccaa tttctttaat taaaaatgca    1260
ataatgaacc gacttaatga ctattattat gctataaagc cgtaa                    1305

<210> SEQ ID NO 3
<211> LENGTH: 434
<212> TYPE: PRT
<213> ORGANISM: Artificial Sequence
<220> FEATURE:
<223> OTHER INFORMATION: Synthetic: CJ_Pal_F4E

<400> SEQUENCE: 3
```

```
Met Arg Gly Asp Lys Arg Val Thr Thr Asp Phe Leu Lys Glu Ile Val
1               5                   10                  15

Gln Gln Asn Arg Ala Gly Gly Ser Arg Gly Ile Tyr Ser Val Cys Ser
            20                  25                  30

Ala His Arg Leu Val Ile Glu Ala Ser Met Gln Gln Ala Lys Ser Asp
            35                  40                  45

Gly Ser Pro Leu Leu Val Glu Ala Thr Cys Asn Gln Val Asn His Glu
        50                  55                  60

Gly Gly Tyr Thr Gly Met Thr Pro Ser Asp Phe Cys Lys Tyr Val Leu
65                      70                  75                  80

Asp Ile Ala Lys Glu Val Gly Phe Ser Gln Glu Gln Leu Ile Leu Gly
                85                  90                  95

Gly Asp His Leu Gly Pro Asn Pro Trp Thr Asp Leu Pro Ala Ala Gln
            100                 105                 110

Ala Met Glu Ala Ala Lys Lys Met Val Ala Asp Tyr Val Ser Ala Gly
        115                 120                 125

Phe Ser Lys Ile His Leu Asp Ala Ser Met Ala Cys Ala Asp Asp Val
    130                 135                 140

Glu Pro Leu Ala Asp Glu Val Ile Ala Gln Arg Ala Thr Ile Leu Cys
145                 150                 155                 160

Ala Ala Gly Glu Ala Val Ser Asp Lys Asn Ala Ala Pro Met Tyr
                165                 170                 175

Ile Ile Gly Thr Glu Val Pro Val Pro Gly Gly Ala Gln Glu Asp Leu
            180                 185                 190

His Glu Leu Ala Thr Thr Asn Ile Asp Asp Leu Lys Gln Thr Ile Lys
            195                 200                 205

Thr His Lys Ala Lys Phe Ser Glu Asn Gly Leu Gln Asp Ala Trp Asp
        210                 215                 220

Arg Val Ile Gly Val Val Gln Pro Gly Val Glu Phe Asp His Ala
225                 230                 235                 240

Met Val Ile Gly Tyr Gln Ser Glu Lys Ala Gln Thr Leu Ser Lys Thr
                245                 250                 255

Ile Leu Asp Phe Asp Asn Leu Val Tyr Glu Ala His Ser Thr Asp Tyr
            260                 265                 270

Gln Thr Glu Thr Ala Leu Thr Asn Leu Val Asn Asp His Phe Ala Ile
        275                 280                 285

Leu Lys Val Gly Pro Gly Leu Thr Tyr Ala Ala Arg Glu Ala Leu Phe
    290                 295                 300

Ala Leu Ser Tyr Ile Glu Gln Glu Trp Ile Thr Asn Lys Pro Leu Ser
305                 310                 315                 320

Asn Leu Arg Gln Val Leu Glu Glu Arg Met Leu Glu Asn Pro Lys Asn
            325                 330                 335

Trp Ala Lys Tyr Tyr Thr Gly Thr Glu Gln Glu Gln Ala Phe Ala Arg
            340                 345                 350

Lys Tyr Ser Phe Ser Asp Arg Ser Arg Tyr Tyr Trp Ala Asp Pro Ile
        355                 360                 365

Val Asp Gln Ser Val Gln Thr Leu Ile Asn Asn Leu Thr Glu Gln Pro
    370                 375                 380

Ala Pro Met Thr Leu Leu Ser Gln Phe Met Pro Leu Gln Tyr Ala Ala
385                 390                 395                 400

Phe Arg Ala Gly Gln Leu Asn Asn Asp Pro Leu Ser Leu Ile Arg His
            405                 410                 415
```

-continued

```
Trp Ile Gln Glu Val Val Ser Thr Tyr Ala Arg Ala Ser Gly Leu Ala
            420                 425                 430
Val Lys

<210> SEQ ID NO 4
<211> LENGTH: 1305
<212> TYPE: DNA
<213> ORGANISM: Artificial Sequence
<220> FEATURE:
<223> OTHER INFORMATION: Synthetic: CJ_Pal_F4E

<400> SEQUENCE: 4
atcagaggag ataaaagggt gactacagat tttctgaaag aaattgttca acaaaacaga      60
gccggtggta gcagaggtat ttactctgtt tgttctgcgc atcgccttgt tattgaagcg     120
tctatgcagc aagccaaaag cgatggctca ccactgttag tagaggcaac atgtaatcag     180
gttaatcacg aaggtggtta taccggtatg accccaagcg acttttgcaa atacgtgtta     240
gatattgcaa aagaagtggg cttttcccaa gagcaactta ttttaggggg cgaccactta     300
gggcctaacc cgtggactga cctaccagct gcacaggcaa tggaagcggc caaaaaaatg     360
gttgctgatt acgtaagtgc gggcttttca aaaatacatt tagatgcaag catggcatgt     420
gcagatgatg tagagccgct tgctgatgag gttatagcgc agcgcgccac tattttatgt     480
gctgccggcg aagctgctgt tagcgataaa aatgcagccc caatgtatat tattggtacc     540
gaagtgccgg taccaggtgg cgcacaagaa gatttacacg aacttgctac aaccaatatt     600
gatgatttaa acaaaccat taaacccat aaagcaaaat ttagcgaaaa cggtttgcaa       660
gacgcatggg atagagtaat tggtgtagta gtgcagcctg tgttgagtt tgaccacgcg     720
atggtaattg gctatcaaag cgaaaaagca caaacactaa gtaaaactat tttagatttt     780
gataaatttgg tttatgaagc gcattcaacc gattatcaaa ccgaaacagc gttaactaac     840
ttggttaacg accactttgc tattttaaaa gtgggcccag gcttacttta tgcagcgcgc     900
gaagcgttgt ttgcacttag ttatattgag caagagtgga taaccaataa gcctctttct     960
aatttgcgcc aagtgcttga agagcgcatg ctcgaaaacc ctaaaaactg ggctaagtat    1020
tacacaggta cagagcaaga gcaggccttt gcacgaaaat atagctttag cgatagatcg    1080
cgttactatt gggccgatcc tattgttgat caaagtgttc aaacactcat taataactta    1140
actgagcagc cagcgccaat gaccttgctg agtcaattta tgccacttca atatgcggca    1200
tttcgtgcag gacaattaaa taacgatccg cttctttga tcagacactg gatccaagaa     1260
gttgtatcaa cctacgcccg cgctagcgga cttgcagtaa aatag                    1305
```